United States Patent [19]

Wise et al.

[11] 4,218,456
[45] Aug. 19, 1980

[54] 1-(4-FLUOROPHENYL)-4-(1,2,3,6-TETRAHYDRO-4-PHENOXY-1-PYRIDINYL)-BUTANONES

[75] Inventors: Lawrence D. Wise, Ann Arbor, Mich.; Patrick F. Flynn, Wilmington, Del.; Glenn C. Morrison, Ann Arbor, Mich.

[73] Assignee: Warner-Lambert Company, Morris Plains, N.J.

[21] Appl. No.: 922,512

[22] Filed: Jul. 10, 1978

[51] Int. Cl.² .................... A61K 31/44; C07D 213/04
[52] U.S. Cl. .................................... 424/263; 546/301
[58] Field of Search ..................... 546/301; 424/263

[56] References Cited

U.S. PATENT DOCUMENTS 4,128,552  12/1978  Wise et al. ............................. 546/294
4,134,982  1/1979   Wise et al. ............................. 424/263

Primary Examiner—Alan L. Rotman
Attorney, Agent, or Firm—Albert H. Graddis; George M. Kaplan

[57] ABSTRACT

Tetrahydropyridylbutyrophenones of the following formula I:

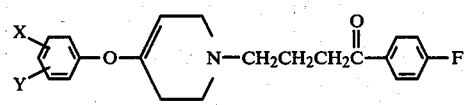

wherein x is hydrogen, halogen such as fluorine, chlorine, bromine or iodine, trifluoromethyl, alkoxy, thioalkoxy, nitro, cyano, amino, lower alkyl of 1 to 6 carbons, aryl or substituted aryl; and y is hydrogen or halogen; and the non-toxic, pharmaceutically acceptable acid addition salts thereof. The compounds of the invention having the formula I are useful in the treatment of psychotic disorders such as schizophrenia.

12 Claims, No Drawings

1-(4-FLUOROPHENYL)-4-(1,2,3,6-TETRAHYDRO-4-PHENOXY-1-PYRIDINYL)-BUTANONES

This invention relates to tetrahydropyridyl-butyrophenones of the formula I:

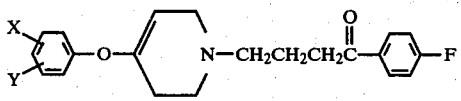

wherein x is hydrogen, halogen such as fluorine, chlorine, bromine or iodine, trifluoromethyl, alkoxy, thioalkoxy, nitro, cyano, amino, lower alkyl of 1–6 carbons, aryl or substituted aryl; and y is hydrogen or halogen; and the non-toxic, pharmaceutically acceptable acid addition salts thereof.

The preferred compounds of this invention are those having the formula I wherein x is hydrogen, halogen, trifluoromethyl, alkoxy, thioalkoxy or lower alkyl; and y is hydrogen or halogen; and the non-toxic, pharmaceutically acceptable acid addition salts thereof.

The compounds of the invention having the formula I are prepared starting with an appropriate 4-phenoxypyridine of formula II:

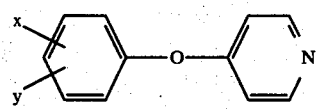

(wherein x and y are as defined above in formula I), which is reduced to its corresponding 1,2,3,6-tetrahydropyridine (formula III below wherein x and y are as defined above for formula I) with aluminum hydride in an appropriate solvent such as ether or tetrahydrofuran.

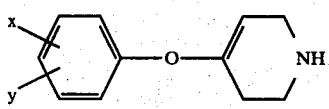

Alkylation of the 1,2,3,6-tetrahydropyridine III with γ-halo-p-fluorobutyrophenone, typically with γ-chloro-p-fluorobutyrophenone, provides the desired compound I. The alkylation reaction is conducted either without an additional solvent or using an appropriate organic solvent such as toluene.

The pharmacologically acceptable acid addition salts of the compounds of this invention are prepared by treating compounds I or III with an acid such as hydrochloric, hydrogen iodide, nitric, sulfuric, oxalic, butenedioc, tartaric and the like in stoichiometric amounts. Of course, the butenedioc acid salts are preferred. These salts are recovered by methods known in the art.

The starting material, 4-phenoxypyridine II, is prepared according to the general method described by Butler, D. E., et al. in J. Med. Chem. 14: 575 (1974), by reacting an appropriately substituted phenol with 4-chloro-pyridine.

In the above definitions for x and y, halogen is meant to include all four members, i.e., fluorine, chlorine, bromine and iodine. Lower alkyl and the lower alkyl portion of lower alkoxy are meant to include 1 to 6 carbon atom chains, preferably 1 to 3 carbon atom chains as exemplified by methyl, ethyl, propyl, isopropyl and so on. Aryl is preferably an aromatic hydrocarbon of 6 to 10 carbon atoms such as phenyl or naphthyl, which may be optionally substituted by groups such as the aforesaid halogen, nitro, amino, lower alkyl or lower alkoxy.

The compounds of the present invention having the formula I exhibit interesting and significant activity as antipsychotics (i.e. for the treatment of schizophrenia). As with other known antipsychotics, the compounds of formula I readily displace $^3$H-haloperidol from dopamine receptor binding sites in the $^3$H-Haloperidol Receptor Binding Assay (HRBA). This screen is a most effective in vitro method for detecting neuroleptic agents and correlates well with human clinical doses. The HRBA screen is described by I. Creese, D. R. Burt and S. H. Snyder, Science, 192, 481 (1976) and P. Seeman, T. Lee, M. Chan-Wong and K. Wong, Nature, 261, 717 (1976). The compound of the present invention having the formula I, in which x is parafluoro and y is hydrogen (Example 9), when tested in aforementioned HRBA screen, showed an 87% inhibition of $^3$H-haloperidol at $10^{-8}$ mol/L. concentration in vitro.

Thus, the compounds of the invention are indicated in the management of psychotic disorders such as schizophrenia in mammals. Generally, a dose of 1 to 100 mg., orally or by injection, once or twice a day is suggested. This dosage regimen for psychotherapeutic effect may be varied depending upon the severity of the condition, the age, weight or sex of the host, and the route of administration.

The compounds of this invention are formulated into dosage forms suitable for oral administration, such as tablets and syrup, by methods well-known to the pharmacist's art. They can also be administered in the form of suppositories, which are also formulated by methods well known to the pharmaceutical art. For parenteral administration, the salts of the above compounds are preferable. They are formulated by dissolving the salt in water, sterilizing and packaging into individual ampules.

To further illustrate the practice of this invention, the following Examples are included:

EXAMPLE 1

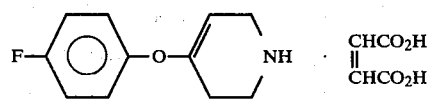

4-(4-Fluorophenoxy)-1,2,3,6-tetrahydropyridine(Z)-2-Butenedioate

To a suspension of 30.0 g of lithium aluminum hydride in 300 ml of ether is slowly added a solution of 33.4 g of aluminum chloride in 500 ml of ether. After the mixture has stirred for 30 minutes, a solution of 91.0 g of 4-(4-fluorophenoxy)pyridine in 500 ml of ether is cautiously added. The mixture is allowed to stir at room temperature for 18 hours after which the excess aluminum hydride is destroyed by careful addition of water. The mixture is filtered, and the filtrate is evaporated. Distillation of the residue gives 77.1 g of colorless oil, b.p. 132°–138° C. (9.0 mm). The maleate salt is generated in ether to yield a tan powder, m.p. 157°–159° C.

Recrystallization from ethanol gives an analytical sample, m.p. 158°–159° C.

Anal. Calcd. for $C_{11}H_{12}FNO.C_4H_4O_4$: C, 58.25; H, 5.21; F, 6.14; N, 4.53. Found: C, 58.26; H, 5.45; F, 5.90; N, 4.61.

EXAMPLE 2

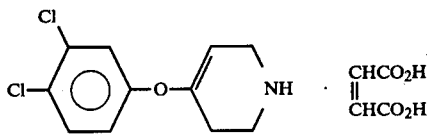

4-(3,4-Dichlorophenoxy)-1,2,3,6-tetrahydropyridine(Z)-2-Butenedioate

Using the procedure in Example 1, 4-(3,4-dichlorophenoxy)pyridine is reduced to afford an orange oil, b.p. 136°–146° C. (0.20 mm). The maleate salt is generated as a white powder, m.p. 154°–155° C.

Anal. Calcd. for $C_{11}H_{11}Cl_2NO.C_4H_4O_4$: C, 50.02; H, 4.20; Cl, 19.69; N, 3.89. Found: C, 49.96; H, 4.15; Cl, 19.83; N, 3.89.

EXAMPLE 3

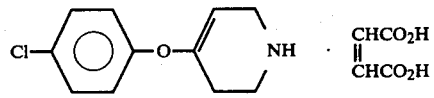

4-(4-Chlorophenoxy)-1,2,3,6-tetrahydropyridine(Z)-2-Butenedioate

Using the procedure in Example 1, 4-(4-chlorophenoxy)pyridine is reduced to give a colorless oil, b.p. 108°–110° C. (0.20 mm). The maleate salt is formed as a tan powder, m.p. 156°–157° C.

Anal. Calcd. for $C_{11}H_{12}ClNO.C_4H_4O_4$: C, 55.31; H, 4.95; Cl, 10.88; N, 4.30. Found: C, 55.31; H, 4.86; Cl, 11.03; N, 4.33.

EXAMPLE 4

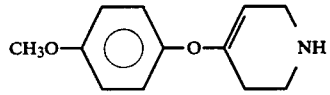

4-(4-Methoxyphenoxy)-1,2,3,6-tetrahydropyridine

Using the procedure in Example 1, 4-(4-methoxyphenoxy)pyridine is reduced to give a colorless oil, b.p. 126°–128° C. (0.5 mm). The product is crystallized from hexane to give a white powder, m.p. 45°–46° C.

Anal. Calcd. for $C_{12}H_{15}NO_2$: C, 70.22; H, 7.37; N, 6.82. Found: C, 70.33; H, 7.44; N, 6.53.

EXAMPLE 5

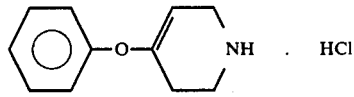

4-Phenoxy-1,2,3,6-tetrahydropyridine Hydrochloride

Using the procedure in Example 1, 4-phenoxypyridine is reduced to yield a yellow oil, b.p. 146°–154° C. (12 mm). The hydrochloride salt is formed as a white powder, m.p. 143°–145° C.

Anal. Calcd. for $C_{11}H_{13}NO.HCl$: C, 62.41; H, 6.67; Cl, 16.75; N, 6.62. Found: C, 62.09; H, 6.64; C, 16.02; N, 6.51.

EXAMPLE 6

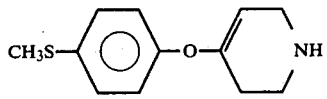

4-[4-(Methylthio)phenoxy]-1,2,3,6-tetrahydropyridine

Using the procedure in Example 1, 4-[4-(methylthio)phenoxy]pyridine is reduced to give a yellow oil, b.p. 152°–156° C. (0.45 mm).

EXAMPLE 7

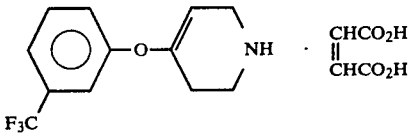

4-[3-(Trifluoromethyl)phenoxy]-1,2,3,6-tetrahydropyridine(Z)-2-Butenedioate

Using the procedure in Example 1, 4-[3-(trifluoromethyl)phenoxy]-pyridine is reduced to yield a colorless oil, b.p. 95°–99° C. (0.70 mm). The maleate salt is formed as a white powder, m.p. 118°–119° C.

Anal. Calcd. for $C_{12}H_{12}F_3NO.C_4H_4O_4$: C, 53.49; H, 4.49; F, 15.86; N, 3.90. Found: C, 53.40; H, 4.75; F, 15.83; N, 4.01.

EXAMPLE 8

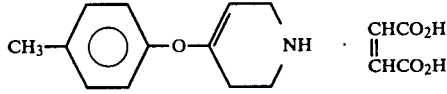

4-(4-Methylphenoxy)-1,2,3,6-tetrahydropyridine(Z)-2-Butenedioate

Using the procedure in Example 1, 4-(4-methylphenoxy)pyridine is reduced to yield a yellow oil, b.p. 113°–120° C. (0.60 mm). The maleate salt is formed as a tan powder, m.p. 126°–128° C.

Anal. Calcd. for $C_{12}H_{15}NO.C_4H_4O_4$: C, 62.94; H, 6.27; N, 4.59. Found: C, 62.91; H, 6.24; N, 4.71.

EXAMPLE 9

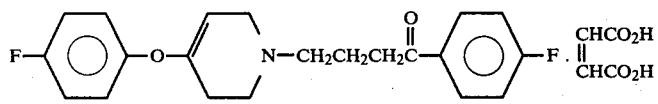

4-[4-(4-Fluorophenoxy)-1,2,3,6-tetrahydro-1-pyridinyl]-1-(4-fluorophenyl)-1-butanone(Z)-2-Butenedioate A mixture of 38.6 g of 4-(4-fluorophenoxy)-1,2,3,6-tetrahydropyridine and 20.1 g of γ-chloro-p-fluorobutyrophenone is heated at 110° C. for 18 hours. The reaction mixture is cooled to room temperature. Ether is added and the suspension is washed well with water. The organic extracts are dried over anhydrous sodium sulfate and evaporated. The residue is distilled to give 21.6 g of viscous oil, b.p. 184°–190° C. (0.20 mm). The maleate is generated in ether to afford 25.4 g of white powder, m.p. 123°–125° C. Recrystallization from acetonitrile gives an analytical sample, m.p. 126°–127° C.

Anal. Calcd. for $C_{21}H_{21}F_2NO_2.C_4H_4O_4$: C, 63.42; H, 5.32; F, 8.03; N, 2.96. Found: C, 63.41; H, 5.31; F, 8.05; N, 2.89.

EXAMPLE 10

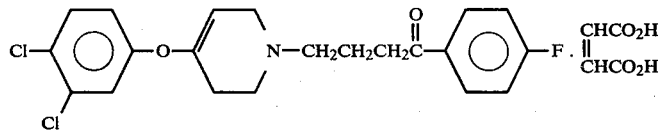

4-[4-(3,4-Dichlorophenoxy)-1,2,3,6-tetrahydro-1-pyridinyl]-1-(4-fluorophenyl)-1-butanone(Z)-2-Butenedioate Using the procedure in Example 9, 4-(3,4-dichlorophenoxy)-1,2,3,6-tetrahydropyridine is reacted with γ-chloro-p-fluorobutyrophenone. Purification of the product by HPLC followed by formation of the maleate gives a yellow powder, m.p. 123°–127° C. Recrystallization from ethyl acetate yield an analytical sample, m.p. 133°–134° C.

Anal. Calcd. for $C_{21}H_{20}Cl_2FNO_2.C_4H_4O_4$: C, 57.26; H, 4.61; Cl, 13.52; F, 3.62; N, 2.67. Found: C, 57.21; H, 4.71; Cl, 13.75; F, 3.49; N, 2.81.

EXAMPLE 11

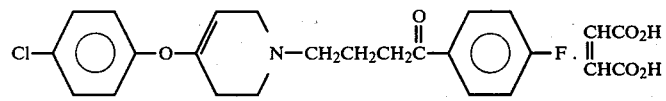

4-[4-(4-Chlorophenoxy)-1,2,3,6-tetrahydro-1-pyridinyl]-1-(4-fluorophenyl)-1-butanone(Z)-2-Butenedioate Using the procedure in Example 9, 4-(4-chlorophenoxy)-1,2,3,6-tetrahydropyridine is reacted with γ-chloro-p-fluorobutyrophenone. Purification of the product by HPLC followed by formation of the maleate gives a white powder, m.p. 96°–100° C. Recrystallization from ethyl acetate yields an analytical sample, m.p. 114°–116° C.

Anal. Calcd. for $C_{21}H_{21}ClFNO_2.C_4H_4O_4$: C, 61.29; H, 5.14; Cl, 7.24; F, 3.88; N, 2.86. Found: C, 61.36; H, 5.04; Cl, 7.50; F, 3.65; N, 2.90.

EXAMPLE 12

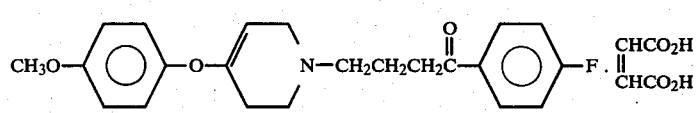

1-(4-Fluorophenyl)-4-[1,2,3,6-tetrahydro-4-(4-methoxyphenoxy)-1-pyridinyl]-1-butanone(Z)-2-Butenedioate Using the procedure in Example 9, 4-(4-methoxyphenoxy)-1,2,3,6-tetrahydropyridine is reacted with γ-chloro-p-fluorobutyrophenone. Purification of the product by HPLC followed by formation of the maleate affords a white powder, m.p. 101°–102° C. Recrystallization from isopropanol gives white crystals, m.p. 102°—103° C.

Anal. Calcd. for $C_{22}H_{24}FNO_3.C_4H_4O_4$: C, 64.59; H, 5.84; F, 3.93; N, 2.90. Found: C, 64.28; H, 5.81; F, 4.18; N, 2.84.

EXAMPLE 13

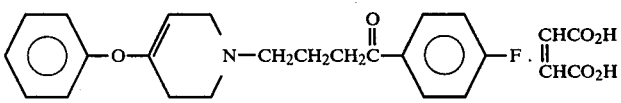

1-(4-Fluorophenyl)-4-(1,2,3,6-tetrahydro-4-phenoxy-1-pyridinyl)-1-butanone(Z)-2-Butenedioate A solution of 13.1 g of 4-phenoxy-1,2,3,6-tetrahydropyridine and 7.52 g of γ-chloro-p-fluorobutyrophenone in 100 ml of toluene is refluxed for 8 hours. The resulting mixture is cooled to room temperature and washed well with water. The organic extracts are dried over anhydrous sodium sulfate and evaporated. The residual oil is purified using a Water's 500 HPLC with two columns. Elution with ethyl acetate affords 6.0 g of yellow oil. The maleate is formed in ether to give 6.60 g of off-white powder, m.p. 130°–133° C. Recrystallization from ethyl acetate three times gives an analytical sample, m.p. 133°–134° C.

Anal. Calcd. for $C_{21}H_{22}FNO_2 \cdot C_4H_4O_4$: C, 65.92; H, 5.75; F, 4.17; N, 3.08. Found: C, 65.83; H, 5.74; F, 4.23; N, 3.09.

EXAMPLE 14

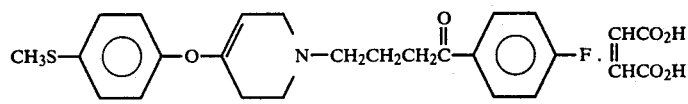

1-(4-Fluorophenyl)-4-[1,2,3,6-tetrahydro-4-[4-(methylthio)-phenoxy]-1-pyridinyl]-1-butanone(Z)-2-Butenedioate Using the procedure in Example 13, 4-[4-(methylthio)phenoxy]-1,2,3,6-tetrahydropyridine is reacted with γ-chloro-p-fluoro-butyrophenone to give a tan powder, m.p. 114°–116° C.

Anal. Calcd. for $C_{22}H_{24}FNO_2 \cdot C_4H_4O_4$: C, 62.26; H, 5.63; N, 2.79; S, 6.39. Found: C, 62.42; H, 5.59; N, 2.85; S, 6.38.

EXAMPLE 15

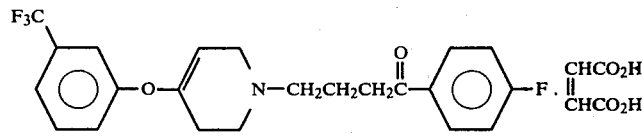

1-(4-Fluorophenyl)-4-[1,2,3,6-tetrahydro-4-[3-(trifluoromethyl)phenoxy]-1-pyridinyl]-1-butanone(Z)-2-Butenedioate Using the procedure in Example 13, 4-[3-(trifluoromethyl)phenoxy]-1,2,3,6-tetrahydropyridine is reacted with γ-chloro-p-fluorobutyrophenone to afford a tan powder, m.p. 143°–144° C.

Anal. Calcd. for $C_{22}H_{21}F_4NO_2 \cdot C_4H_4O_4$: C, 59.66; H, 4.81; F, 14.52; N, 2.68. Found: C, 59.47; H, 4.90; F, 14.53; N, 2.71.

EXAMPLE 16

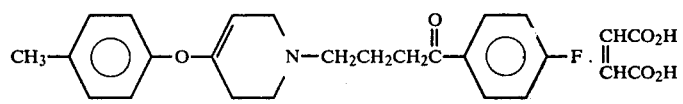

1-(4-Fluorophenyl)-4-[1,2,3,6-tetrahydro-4-(4-methylphenoxy)-1-pyridinyl]-1-butanone(Z)-2-Butenedioate Using the procedure in Example 13, 4-(4-methylphenoxy)-1,2,3,6-tetrahydropyridine is reacted with γ-chloro-p-fluorobutyrophenone to give a tan powder, m.p. 113°–114° C.

Anal. Calcd. for $C_{22}H_{24}FNO_2 \cdot C_4H_4O_4$: C, 66.51; H, 6.01; F, 4.05; N, 2.98. Found: C, 66.21; H, 5.95, F, 4.18; N, 2.98.

We claim:

1. A compound having the formula I:

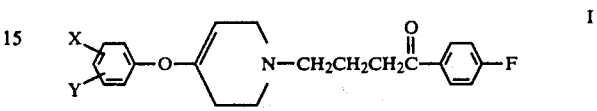

wherein x is hydrogen, halogen, trifluoromethyl, lower alkoxy, lower thioalkoxy, nitro, amino, lower alkyl, phenyl, phenyl substituted by halogen, nitro, amino, lower alkyl, or lower alkoxy; naphthyl, naphthyl substituted by halogen, nitro, amino, lower alkyl or lower alkoxy; and y is hydrogen or halogen, and the non-toxic, pharmaceutically acceptable, acid addition salts thereof.

2. A compound according to claim 1 wherein x is hydrogen, halogen, trifluoromethyl, lower alkoxy, lower thioalkoxy or lower alkyl; and y is hydrogen or halogen; and the non-toxic, pharmaceutically acceptable, acid addition salts thereof.

3. The compound according to claim 1 which is 4-[4-(4-fluorophenoxy)-1,2,3,6-tetrahydro-1-pyridinyl]-1-(4-fluorophenyl)-1-butanone(Z)-2-butenedioate.

4. The compound according to claim 1 which is 4-[4-(3,4-dichlorophenoxy)-1,2,3,6-tetrahydro-1-pyridinyl]-1-(4-fluorophenyl)-1-butanone(Z)-2-butenedioate.

5. The compound according to claim 1 which is 4-[4-(4-chlorophenoxy)-1,2,3,6-tetrahydro-1-pyridinyl]-1-(4-fluorophenyl)-1-butanone(Z)-2-butenedioate.

6. The compound according to claim 1 which is 1-(4-fluorophenyl)-4-[1,2,3,6-tetrahydro-4-(4-methoxyphenoxy)-1-pyridinyl]-1-butanone(Z)-2-butenedioate.

7. The compound according to claim 1 which is 1-(4-fluorophenyl)-4-(1,2,3,6-tetrahydro-4-phenoxy-1-pyridinyl)-1-butanone(Z)-2-butenedioate.

8. The compound according to claim 1 which is 1-(4-fluorophenyl)-4-[1,2,3,6-tetrahydro-4-[4-(methylthio)-phenoxy]-1-pyridinyl]-1-butanone(Z)-2-butenedioate.

9. The compound according to claim 1 which is 1-(4-fluorophenyl)-4-[1,2,3,6-tetrahydro-4-[3-(trifluoromethyl)-phenoxy]-1-pyridinyl]-1-butanone(Z)-2-butenedioate.

10. The compound according to claim 1 which is 1(4-fluorophenyl)-4-[1,2,3,6-tetrahydro-4-(4-methylphenoxy)-1-pyridinyl]-1-butanone(Z)-2-butenedioate.

11. A pharmaceutical composition for the treatment of manifestations of psychotic disorders in mammals comprising a psychotherapeutically effective amount of a compound according to claim 1 having the formula I together with an inert pharmaceutical carrier therefor.

12. A method for treating the manifestations of psychotic disorders in mammals which comprises the administration of a psychotherapeutically effective amount of a compound according to claim 1 having the formula I.

* * * * *